United States Patent
Lanos et al.

(10) Patent No.: US 10,351,895 B2
(45) Date of Patent: Jul. 16, 2019

(54) BIOLOGICAL DOSAGE OF PEPTIDOGLYCANS

(71) Applicant: ROQUETTE FRERES, Lestrem (FR)

(72) Inventors: Pierre Lanos, La Bassee (FR); Marc Biguet, Neuve Chapelle (FR); Roselyne Bernard, Lestrem (FR); Fabrice Allain, Lille (FR); Mathieu Carpentier, Saint Andre lez Lille (FR); Agnès Denys, Lille (FR); Héla Hacine-Gherbi, Villeneuve d'Ascq (FR)

(73) Assignee: Roquette Freres, Lestrem (FR)

( * ) Notice: Subject to any disclaimer, the term of this patent is extended or adjusted under 35 U.S.C. 154(b) by 53 days.

(21) Appl. No.: 15/116,852

(22) PCT Filed: Feb. 5, 2015

(86) PCT No.: PCT/FR2015/050275
§ 371 (c)(1),
(2) Date: Aug. 5, 2016

(87) PCT Pub. No.: WO2015/118267
PCT Pub. Date: Aug. 13, 2015

(65) Prior Publication Data
US 2017/0081699 A1    Mar. 23, 2017

(30) Foreign Application Priority Data
Feb. 7, 2014   (FR) .................... 14 50966

(51) Int. Cl.
C12Q 1/37    (2006.01)
C12Q 1/34    (2006.01)
C12Q 1/02    (2006.01)
C12Q 1/22    (2006.01)
G01N 33/68   (2006.01)

(52) U.S. Cl.
CPC ............ *C12Q 1/34* (2013.01); *C12Q 1/02* (2013.01); *C12Q 1/22* (2013.01); *G01N 33/6863* (2013.01); *G01N 2333/936* (2013.01)

(58) Field of Classification Search
CPC ...................................................... C12Q 1/37
See application file for complete search history.

(56) References Cited

U.S. PATENT DOCUMENTS

2009/0317838 A1   12/2009  Cavaillion et al.
2013/0095094 A1   4/2013   Erridge
2014/0051097 A1   2/2014   Lanos et al.
(Continued)

FOREIGN PATENT DOCUMENTS

FR   2 978 774     2/2013
GB   2481267       12/2011
(Continued)

OTHER PUBLICATIONS

Nakimbugwe et al., "Cell wall substrate specificity of six different lysozymes and lysozyme inhibitory activity of bacterial extracts," FEMS Microbiol Lett 259:41-46, 2006.*
(Continued)

*Primary Examiner* — Rosanne Kosson (57) ABSTRACT

The present invention relates to a biological method for the dosage of peptidoglycans in a sample, especially a sample of glucose polymers.

10 Claims, 5 Drawing Sheets

(56) References Cited

U.S. PATENT DOCUMENTS

2015/0125871 A1  5/2015  Duvet et al.
2016/0054301 A1  2/2016  Lanos et al.

FOREIGN PATENT DOCUMENTS

WO   WO 2009/115533   9/2009
WO   WO 2012/143647   10/2012
WO   WO 2013/178931   12/2013
WO   WO 2014/154651   10/2014

OTHER PUBLICATIONS

Erridge, C. "The capacity of foodstuffs to induce innate immune activation of human monocytes in vitro is dependent on food content of stimulants of Toll-like receptors 2 and 4" *British Journal of Nutrition*, 2011, pp. 15-23, vol. 105.

Glorieux, G. et al. "A novel bio-assay increases the detection yield of microbiological impurity of dialysis fluid, in comparison to the LAL-test" *Nephrology Dialysis Transplantation*, Feb. 1, 2009, pp. 548-554, vol. 24, No. 2.

Huang, L.-Y. et al. "Use of Toll-Like Receptor Assays to Detect and Identify Microbial Contaminants in Biological Products" *Journal of Clinical Microbiology*, Nov. 1, 2009, pp. 3427-3434, vol. 47, No. 11.

Written Opinion in International Application No. PCT/FR2015/050275, dated May 22, 2015, pp. 1-6.

\* cited by examiner

BIOLOGICAL DOSAGE OF PEPTIDOGLYCANS

CROSS-REFERENCE TO RELATED APPLICATION

This application is the U.S. national stage application of International Patent Application No. PCT/FR2015/050275, filed Feb. 5, 2015.

FIELD OF THE INVENTION

The present invention relates to an assay of peptidoglycans in a sample, in particular a sample of glucose polymers.

CONTEXT OF THE INVENTION

Aseptic inflammatory episodes are major complications observed during treatments using products manufactured for therapeutic purposes (for example: peritoneal dialysis, parenteral nutrition, injection by the venous route).

Although some of these inflammatory episodes are connected with a problem of a chemical nature (accidental presence of chemical contaminants or incorrect dosages of certain compounds), most cases result from the presence of contaminants of microbial origin released during the manufacturing processes.

It is now clearly established that lipopolysaccharides (LPSs) and peptidoglycans (PGNs) are the main contaminants having a high risk of triggering such inflammatory episodes when they are present at trace levels in manufactured products.

The LAL (Limulus Amebocyte Lysate) assay is used routinely by many quality control laboratories for detecting and assaying contaminations with LPS. This assay is based on recognition of the endotoxins by a sensing complex extracted from Limulus hemolymph.

Other assays also based on the reactivity of extracts of invertebrate hemolymph are currently proposed for detecting PGNs in products for therapeutic use (SLP-Wako, Immunetics).

However, these assays have the disadvantage that they are not very specific, since they also react with other molecules of microbial origin, such as β-glucans.

In addition, these methods require purchasing special equipment for this use, which greatly increases the costs and therefore limits access to these assay techniques.

Moreover, LPSs and PGNs have variable structures depending on their bacterial origin, which is responsible for large differences in inflammatory reactivity.

That is why it is in addition necessary to express the results of the assays in equivalent units of standard molecules (for example, LPS of *E. coli* in the LAL assay).

Moreover, these molecules are most often present in the form of macromolecular complexes, which affects their solubility and their inflammatory potential.

For example, the PGNs are very variable in size and are often aggregated with other molecules of the bacterial walls, such as lipoteichoic acids and lipopeptides.

Thus, "biological" methods have been developed to take account solely of the inflammatory load associated with these molecules.

The effector cells of the inflammatory response possess special sensors for recognition of molecular structures specifically produced by infectious agents.

These molecules, called PAMPs for pathogen-associated molecular pattern molecules, are essentially recognized by TLRs (Toll-like receptors) and NLRs (Nod-like receptors), whose specificity is related to the molecular structure of the different classes of inflammatory molecules.

In contrast to LPSs, which are ligands recognized by TLR4 type receptors, PGNs are detected by TLR2 type membrane receptors, while the final depolymerization products thereof are recognized by the intracellular receptor NOD2.

In recent years, in vitro cellular assays have been developed to replace the animal models of inflammatory response.

Most of these assays are based on the incubation of monocyte cells in the presence of the contaminated products and on back-titration assay of the production of inflammatory cytokines (TNF-α, IL-1β, IL-6, IL-8, RANTES).

However, assays using primary cells isolated from blood are subject to considerable inter-individual variability of the donors, which may be responsible for experimental biases.

In contrast, the monocyte cell lines give constant responses, which explains why they are generally preferred to primary cells. However, these lines are not completely satisfactory either.

For example, the choice of cytokines is often criticized, as most are expressed transiently and their concentration in the culture medium does not always reflect the real load of inflammatory molecules.

Since all the monocyte cells express the majority of the TLRs/NLRs, assays based on their use are not selective for one type of contaminant, but will give an overall inflammatory response.

Moreover, the main problem arises from the differences in sensitivity of the cells with respect to the different inflammatory molecules.

Thus, the PGNs, TLR2 ligands, are far less reactive than the LPSs, which makes them difficult to detect by these approaches.

In fact, the LPSs induce a significant response for concentrations of the order of a ng/ml, whereas 100 times higher concentrations of PGN are necessary to obtain a similar response (w/w ratio).

For some years, transfected cell lines have been proposed for replacing the above models in biological assays for detecting and quantifying the reactivity of inflammatory compounds.

These noninflammatory lines (for example: HEK-293) are stably transfected by a gene coding for a specific receptor of a class of inflammatory agonists.

They also contain an expression vector for a reporter gene coding for an enzyme (for example, luciferase or alkaline phosphatase), whose synthesis is dependent on activation of the inflammatory receptor.

Thus, recognition of a contaminant by the cells expressing the appropriate receptor will trigger the synthesis of the enzyme, production of which will be followed by conversion of its substrate into a colored or luminescent product.

As this product is easily quantifiable, this method allows rapid assay of the inflammatory response associated with a type of contaminant.

These cellular models have many advantages: replacement of ELISA assays of cytokines with an enzyme assay, high reproducibility in the assays on account of the stable character of the lines, targeting of certain classes of inflammatory molecules as a function of the receptor expressed, detection of contaminants at very low thresholds.

These cellular models may therefore replace the assays of cytokine response in vitro, as they make it possible to specifically target the inflammatory factors that are agonists of a given TLR or NLR, and to quantify the inflammatory response associated with this agonist.

For example, cells specifically expressing TLR2 and TLR4 have already been used for detecting contaminants in food products (works of Clett Erridge of the Department of Cardiovascular Sciences of Leicester University—UK in *British Journal of Nutrition*, Vol. 105/issue 01/January 2011, pp 15-23).

Moreover, companies such as InvivoGen now market a wide range of cells of the HEK-293 line (HEK-Blue™) transfected with the various TLR or NRL receptors.

These cells contain, as reporter, a gene coding for a secreted form of alkaline phosphatase (SEAP: secreted embryonic alkaline phosphatase), which allows quick and easy colorimetric assay of the response to the inflammatory agonists.

These HEK-Blue™ cells have already been used successfully for detecting the presence of contaminants in concentrated solutions of glucose polymer and their synergistic effect (WO2012/143647).

Thus, there is still a constant need to develop alternative improved methods of assaying total PGN in a sample, in particular a sample of glucose polymers.

SUMMARY OF THE INVENTION

The present invention therefore relates to a biological method of assaying peptidoglycans in a sample, in particular a sample of glucose polymers.

In particular, the present invention relates to a method of assaying peptidoglycans (PGNs) in a sample of glucose polymer, comprising:
a) enzymatic treatment of the sample of glucose polymer by an enzyme of lysozyme type;
b) bringing the treated sample or a dilution thereof into contact with a recombinant cell expressing an exogenous TLR2 receptor (Toll-like Receptor 2) and a reporter gene under the direct dependence of the signaling pathway associated with the TLR2 receptor, the reporter gene coding for a colored or fluorescent protein or for a protein whose activity can be measured;
c) measuring the reporter gene signal; and
d) determining the amount of PGN in the sample using a calibration curve of the correspondence between the amount of PGN and the intensity of the reporter gene signal.

Preferably, the enzymatic treatment of the sample makes it possible to fragment and disaggregate the PGNs contained in the sample, in particular so as to make them capable of activating the TLR2 receptor.

In particular, the enzymatic treatment of the sample makes it possible to generate PGNs predominantly having a size of approximately 120 kDa.

Preferably, the enzymatic treatment is carried out by means of an enzyme of lysozyme type, the activity of which is capable of disaggregating the PGN complexes in the sample. Indeed, the present invention is concerned with releasing active PGNs, of sizes between 30 and 5000 kDa, especially of a size of approximately 120 kDa.

Specific enzymatic treatment conditions are chosen to this end.

Preferably, the enzyme is a lysozyme.

In one preferred embodiment, the enzyme is used at a concentration of approximately 50 U/ml to 2500 U/ml and brought into contact with the sample at a glucose polymer concentration of 37.5% (weight/volume) for 10 minutes to 20 h at a temperature of 37° C. Preferably, the enzyme is used at a concentration of approximately 250 U/ml to 2500 U/ml and brought into contact with the sample at a glucose polymer concentration of 37.5% (weight/volume) for 30 minutes to 16 h at a temperature of 37° C.

In a particularly preferred embodiment, the enzyme is lysozyme, used at a concentration of approximately 250 U/ml and brought into contact with the sample at a glucose polymer concentration of 37.5% (weight/volume) for 2 h at a temperature of 37° C.

Then, the sample thus treated will be subjected to the assay with recombinant cells expressing the TLR2 receptor according to the present invention.

Preferably, the recombinant cells expressing the TLR2 receptor have the reporter gene coding for a secreted alkaline phosphatase. In a preferred embodiment, the cell is a cell of the HEK-Blue™ hTLR2 line.

Preferably, the calibration curve of the correspondence between the amount of PGN and the intensity of the reporter gene signal is prepared with PGNs derived from a bacterium selected from *Staphylococcus aureus, Micrococcus luteus, Escherichia coli, Bacillus subtilis* and *Alicyclobacillus acidocaldarius*, preferably from *Staphylococcus aureus, Micrococcus luteus*, and *Alicyclobacillus acidocaldarius*. This calibration curve may be standardized or calibrated using an internal standard that is an agonist of TLR2, preferably a lipopeptide, in particular $PAM_3Cys$-Ser-(Lys)4 trihydrochloride.

In an alternative and preferred manner, the calibration curve of the correspondence between the amount of PGN and the intensity of the reporter gene signal may be prepared using an internal standard that is an agonist of TLR2, preferably a lipopeptide, in particular $PAM_3Cys$-Ser-(Lys)4 trihydrochloride. Indeed, it has been shown by the inventors that, entirely surprisingly, $PAM_3Cys$-Ser-(Lys)4 trihydrochloride makes it possible to calibrate the TLR2 response to the different standard PGNs. Thus, the amount of $PAM_3Cys$-Ser-(Lys)4 trihydrochloride in ng/ml corresponds to the "corrected" amount of PGN in ng/ml. The calibration curve may therefore be set up with $PAM_3Cys$-Ser-(Lys)4 trihydrochloride in an entirely reproducible manner, without needing to rely on standard PGNs which introduce variability depending on their bacterial origin and their method of production.

Optionally, the method comprises a preliminary step of preparation of the calibration curve using an internal standard that is an agonist of TLR2, preferably a lipopeptide, in particular $PAM_3Cys$-Ser-(Lys)4 trihydrochloride.

The invention further relates to a kit for assaying peptidoglycans (PGNs) in a sample of glucose polymers, comprising:
a recombinant cell expressing an exogenous TLR2 receptor (Toll-like Receptor 2) and a reporter gene under the direct dependence of the signaling pathway associated with the TLR2 receptor, the reporter gene coding for a colored or fluorescent protein or for a protein whose activity can be measured; and
either a calibration curve of the correspondence between the amount of PGN and the intensity of the reporter gene signal, or an internal standard that is an agonist of TLR2, preferably a lipopeptide, in particular $PAM_3Cys$-Ser-(Lys)4 trihydrochloride;
optionally, instructions for use, and/or a solution for pretreating the sample, in particular an enzyme of lysozyme type.

In one particular embodiment, the kit comprises:
a recombinant cell expressing an exogenous TLR2 receptor (Toll-like Receptor 2) and a reporter gene under the direct dependence of the signaling pathway associated with the TLR2 receptor, the reporter gene coding for a colored or fluorescent protein or for a protein whose activity can be measured with or without substrate; and an internal standard that is an agonist of TLR2, preferably a lipopeptide, in particular PAM$_3$Cys-Ser-(Lys)4 trihydrochloride;

optionally, instructions for use and/or a lysozyme solution.

DETAILED DESCRIPTION OF THE INVENTION

The present invention therefore relates to a biological method for assaying peptidoglycans in a sample, in particular a sample of glucose polymers.

In particular, the present invention relates to a method of assaying peptidoglycans (PGNs) in a sample of glucose polymer, comprising:
a) enzymatic treatment of the sample of glucose polymer by an enzyme of lysozyme type;
b) bringing the treated sample or a dilution thereof into contact with a recombinant cell expressing an exogenous TLR2 receptor (Toll-like Receptor 2) and a reporter gene under the direct dependence of the signaling pathway associated with the TLR2 receptor, the reporter gene coding for a colored or fluorescent protein or for a protein whose activity can be measured with or without substrate;
c) measuring the reporter gene signal; and
d) determining the amount of PGN in the sample using a calibration curve of the correspondence between the amount of PGN and the intensity of the reporter gene signal.

Preferably, the glucose polymers are intended for peritoneal dialysis, enteral and parenteral nutrition and feeding of neonates.

In a preferred embodiment, the glucose polymers that will be tested are icodextrin or maltodextrins.

In particular, they may be intended for preparation of peritoneal dialysis. They may be tested at one or more stages of their preparation, and especially at the level of the raw material, at any step in their preparation method, and/or at the level of the end product of the method. They may also be tested as a sample of a solution for peritoneal dialysis.

In a first step of the method, the sample of glucose polymer is treated enzymatically.

The aim of this treatment is to fragment the PGNs and/or disaggregate the PGNs contained or trapped in aggregates, the aim being to generate PGNs capable of interacting with the TLR2 receptors and of activating them.

As stated above, this treatment should make it possible to disaggregate the PGNs contained or trapped in aggregates and to fragment the PGNs that are too large, especially to generate soluble PGNs with sizes between 30 and 5000 kDa, especially of approximately 120 kDa.

However, the treatment must not affect the capacity of the PGNs to interact with the TLR2 receptors. It is preferably optimized for releasing a maximum amount of PGNs capable of interacting with TLR2 and of activating the receptor and for storing a maximum amount of PGNs already active on TLR2.

In one embodiment, treatment of the sample at a glucose polymer concentration of 37.5% (weight/volume) is carried out by a lysozyme solution at a temperature of 37° C.

Preferably, the treatment of the sample comprises incubation of the lysozyme at a concentration of approximately 50 U/ml to 2500 U/ml in the sample at a glucose polymer concentration of 37.5% (weight/volume) for 10 minutes to 20 h at a temperature of 37° C.

Of course, if the glucose polymer concentration varies, those skilled in the art should adapt the amount of enzyme and/or the duration of incubation accordingly.

In a preferred embodiment, the treatment of the sample at a glucose polymer concentration of 37.5% (weight/volume) is carried out by a lysozyme solution at a temperature of 37° C. The lysozyme is then used at a concentration of 250 to 2500 U/ml for 30 minutes to 16 h at a temperature of 37° C. Preferably, the lysozyme is used at a concentration of 250 U/ml for 2 h at a temperature of 37° C.

The lysozyme is an enzyme sold, for example, by Euromedex (ref: 5934; origin: egg white; activity: 25 000 units/mg). However, it should be noted that those skilled in the art may also use other lysozymes fulfilling the same criteria of enzyme activity and of degree of purity.

In a subsequent step, the sample and/or dilutions thereof is/are brought into contact with recombinant cells expressing the TLR2 receptor. The cells are qualified as recombinant as these are cells that have been modified by the introduction of a nucleic acid coding for the TLR2 receptor, preferably the human TLR2 receptor, the initial cell not expressing TLR2.

The activity of the TLR2 receptor is detected using a reporter gene that is under the direct dependence of the signaling pathway associated with said receptor. Preferably, this reporter gene codes for a colored or fluorescent protein, or for a protein whose activity can be measured with or without substrate.

In particular, the reporter gene codes for an alkaline phosphatase. The reporter gene may especially produce a secreted form of alkaline phosphatase (SEAP: secreted embryonic alkaline phosphatase), whose synthesis is under the direct dependence of the signaling pathway associated with TLR2.

In a preferred embodiment, the cell line used is an HEK-10 Blue™ line (sold by InvivoGen), modified by stable transfection with vectors coding for human TLR2: the HEK-Blue™ hTLR2 line. However, it should be noted that those skilled in the art may also use other lines commercially available (Imgenex) or they may prepare them.

When the cell is HEK-Blue™ hTLR2, the cell is preferably used at a density of approximately 50 000 cells/well for a 96-well plate.

Next, the method comprises measuring the reporter gene signal.

In a preferred embodiment using the HEK-Blue™ hTLR2 line, the signal is the measure of the activity of alkaline phosphatase. Preferably, the enzymatic reaction is carried out using a 1:3 ratio of medium to be assayed to SEAP reagent (for example 50 μl of medium and 150 μl of SEAP reagent). Moreover, a reaction time of at least 60 minutes will be preferred.

Finally, the amount of PGN in the sample is determined using a calibration curve of the correspondence between the amount of PGN and the intensity of the reporter gene signal.

The PGN standard is preferably calibrated using an internal standard that is an agonist of TLR2, so as to express the results in equivalent units of active PGN.

The internal standard may be a lipopeptide, preferably synthetic, in particular PAM$_3$Cys-Ser-(Lys)4 trihydrochloride (Pam3(cys), PAM or Pam signifying palmitic acid).

Thus, the calibration curve of the correspondence between the amount of PGN and the intensity of the reporter gene signal may be produced directly with an internal standard that is an agonist of TLR2, preferably a lipopeptide, in particular PAM$_3$Cys-Ser-(Lys)4 trihydrochloride, an amount of PAM$_3$Cys-Ser-(Lys)4 trihydrochloride in ng/ml corresponding to the amount of PGN in ng/ml.

In an alternative manner, the calibration curve of the correspondence between the amount of PGN and the intensity of the reporter gene signal may be standardized or calibrated using an internal standard that is an agonist of TLR2, preferably a lipopeptide, in particular PAM$_3$Cys-Ser-(Lys)4 trihydrochloride.

This internal standard is preferably synthetic or has a well-defined structure/composition. The calibration or standardization is carried out by comparing the slopes of the linear portions of each dose-response curve and by calculating a correction factor allowing the curve obtained with the calibration standard and that of the PGN standard to be superimposed.

This curve of the correspondence between the amount of PGN and the intensity of the reporter gene signal may also be obtained with an internal standard that is an agonist of TLR2, preferably a lipopeptide, in particular PAM$_3$Cys-Ser-(Lys)4 trihydrochloride, especially with the same cells, in the same conditions, with increasing doses of TLR2 agonist internal standard.

Just as for PGN, it may be obtained in the absence of or, preferably, in the presence of glucose polymer.

Figure 1:
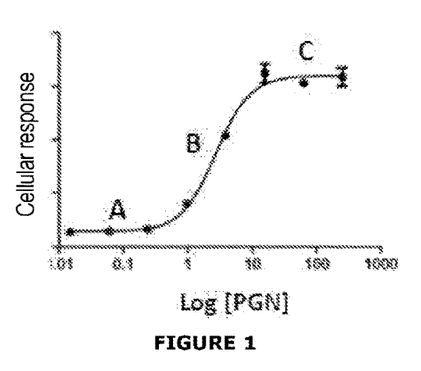
FIG. 1: Theoretical curve of the cellular response as a function of increasing concentrations of PGN.

Typically, the calibration curve is a conventional curve of cellular response of the sigmoid type (FIG. 1).

part (A) corresponds to the responses obtained with low concentrations of PGN, below those giving effective activation of TLR2. This nonlinear zone therefore corresponds to the detection limit threshold of the method. So as to include the variability of the method, this detection threshold is estimated at three times the value of the background noise (response obtained in the absence of a stimulus);

part (B) is the most interesting as a linear response is observed. This zone with effective response makes it possible to determine a direct relationship between the cellular response and the PGN level. This is therefore the assay zone;

part (C) corresponds to saturation of the cellular response in the presence of excessive concentrations of PGN. There is in fact saturation of the TLR2 receptors.

The linear part of the calibration curve is considered, this part corresponding to a zone (part B) in which the amount of PGN is directly proportional to the reporter gene signal.

In the case of samples likely to be heavily contaminated with PGN, it will be necessary to perform several serial dilutions so as to always be located in the zone of linearity. Conversely, low concentrations of PGN require a step of concentration of the sample if it is desired to increase the sensitivity of the assay.

Optionally, the method further comprises an assay with a control cell that does not express TLR2, more generally that does not express an innate immunity receptor. For example, the HEK-Blue™ Null2 line may be used. This is a control line, use of which is useful for verifying that the sample of glucose polymers does not induce production of the enzyme by an intrinsic mechanism.

The present invention also relates to a kit enabling the assaying of peptidoglycans (PGNs) in a sample of glucose polymers, the kit comprising:

a recombinant cell expressing an exogenous TLR2 receptor (Toll-like Receptor 2) and a reporter gene under the direct dependence of the signaling pathway associated with the TLR2 receptor, the reporter gene coding for a colored or fluorescent protein or for a protein whose activity can be measured with or without substrate. The cell is especially preferably the HEK-Blue™ hTLR2 line. As negative control, the kit may also comprise a cell not expressing an innate immunity receptor, for example the HEK-Blue™ Null2 line;

either a calibration curve of the correspondence between the amount of PGN and the intensity of the reporter gene signal, or an internal standard that is an agonist of TLR2, preferably a lipopeptide, in particular PAM$_3$Cys-Ser-(Lys)4 trihydrochloride. Optionally, the kit may comprise a calibration curve and an internal standard that is an agonist of TLR2, preferably a lipopeptide, in particular PAM$_3$Cys-Ser-(Lys)4 trihydrochloride. Alternatively, the kit may comprise a calibration curve and also a calibrated PGN standard derived from the same microorganism as that used to prepare this calibration curve;

optionally, instructions for use, a solution for pretreating the sample, the reagents to be used for measuring the response of the reporter gene, microplates, etc. The kit may especially comprise a lysozyme.

EXAMPLES

The assay is based on the specific recognition of PGNs by a line expressing the TLR2 receptor and on the production of an enzyme activity measurable via activation of the signaling pathway associated with TLR2.

Cellular Material

For the experiments relating to this assay, two lines are used:

HEK-Blue™ hTLR2 (HEK-TLR2) line: specific response for the TLR2 ligands, with strong reactivity for the soluble PGNs.

HEK-Blue™ Null2 (HEK-Null) line: nonspecific response connected with a cytotoxic effect of the sample.

The cells are cultured according to the recommendations of the supplier (InvivoGen). At 75% confluence, the cells are resuspended at a density of 0.28×10$^6$ cells/ml. Before stimulation, 180 μl of the cell suspension are distributed in the culture wells (96-well plate), that is to say 50 000 cells/well. The cells are then stimulated for 24 h by adding 20 μl of the samples of glucose polymer at 37.5% (weight/volume) (i.e. a final dilution of the samples at 3.75%). After 24 h of stimulation, the cellular response is measured by quantification of the enzyme activity produced.

1—Establishment of the Calibration Curve for Biological Assay of PGNs with an Internal Standard The dose-response curves were constructed by diluting the PGNs of different bacterial species in a solution of uncontaminated maltodextrin (referenced P-11.11) prepared at 37.5% (weight/volume). The PGNs assayed are extracted from *Staphylococcus aureus* (Sigma, Cat No 77140), *Micrococcus luteus* (Sigma, Cat No 53243), *Bacillus subtilis* (InvivoGen, # tlrl-pgnb2), *Escherichia coli* K12 (InvivoGen, # tlrl-pgnek) and *Alicyclobacillus acidocaldarius* (strain CNCM I-4689).

Figure 2:
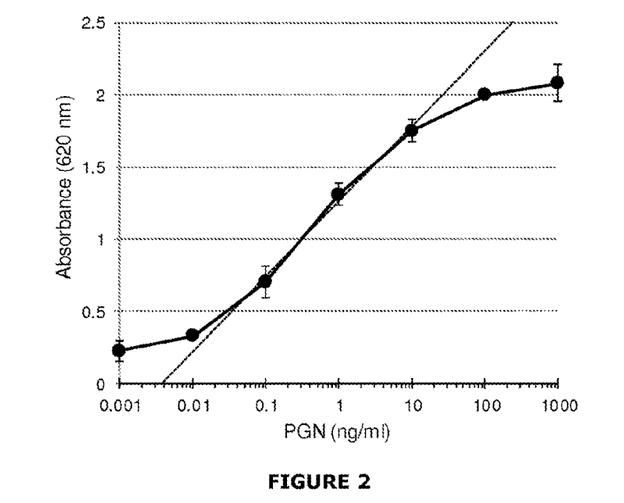
FIG. 2: Calibration curve of the cellular response as a function of the *S. aureus* PGN level obtained with the HEK-Blue™-hTLR2 cells.

The curves obtained are conventional for the responses observed in the assays performed with a cellular material (bioassay) (FIGS. 1 and 2). The absorbance values below 0.2 are evidence of PGN concentrations that are too low to induce a cellular response, whereas values above 2 show a plateau effect connected with saturation of the TLR2 receptors. Consequently, only the zone between these two limit values of absorbance allows correlation of the production of SEAP with the amount of PGN present in the samples.

Figure 3:
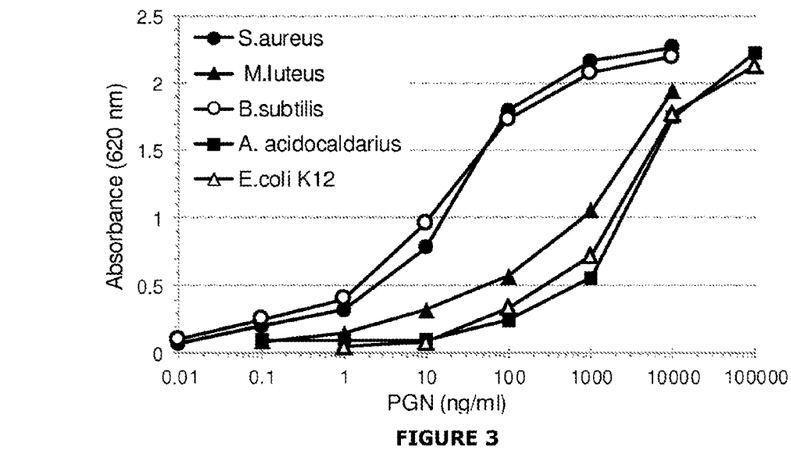
FIG. 3: Response of the HEK-Blue™-hTLR2 cells as a function of increasing concentrations of PGN from different bacterial species.

The responses observed show a large variability in the cellular reactivity associated with each type of PGN. Indeed, the concentrations giving a response equal to 50% of the maximum response (EC50) are ~20 ng/ml for the PGNs of *S. aureus* and *B. subtilis*, 1500 ng/ml for *M. luteus*, and more than 2000 ng/ml for those extracted from *A. acidocaldarius* and *E. coli* K12 (FIG. 3).

However, these differences were expected, since the PGNs have different structures depending on their bacterial origin, which is responsible for large variations in inflammatory reactivity. These observations emphasize the importance of defining an internal standard so as to be able to express the results in equivalent units of PGN.

Another factor likely to alter the response of the HEK-TLR2 cells is the size of the PGNs, which will influence their solubility and reactivity with respect to TLR2. Thus, the procedure for purification of these macromolecules may have a considerable influence on the response of the cells, since the conditions of extraction could alter the size of the PGNs, or even cause partial degradation.

It therefore seems necessary to introduce an internal standard for the calibration curve, so as to avoid errors relating to the variability of the PGNs and to express the results as amount of "active" PGN.

Figure 4:
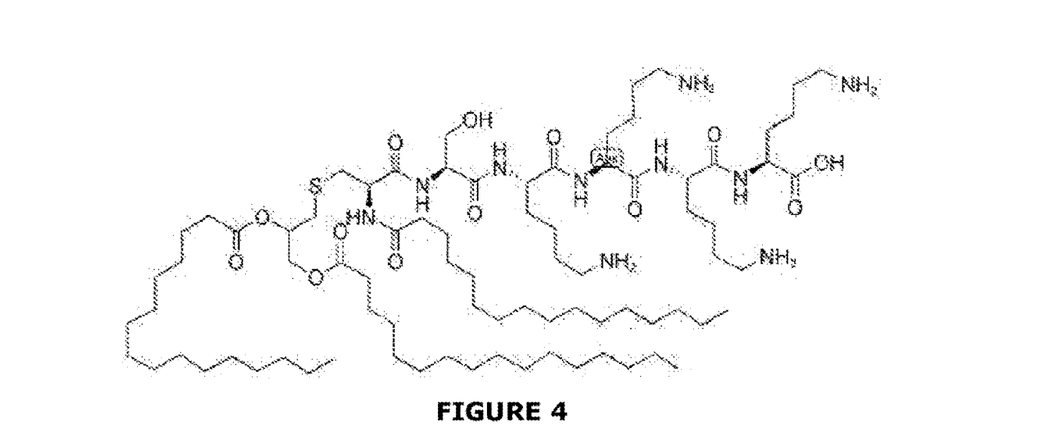
FIG. 4: Structure of PAM$_3$Cys-Ser-(Lys)4 trihydrochloride (PAM3(cys)).

PAM$_3$Cys-Ser-(Lys)4 trihydrochloride (PAM$_3$(cys)) is a triacylated synthetic lipopeptide that mimics the structure of the bacterial lipopeptides and acts as a strong agonist of TLR2. Being of homogeneous structure, it is often used as positive control for calibrating the responses of cells expressing the TLR2 receptor (FIG. 4).

Figure 5:
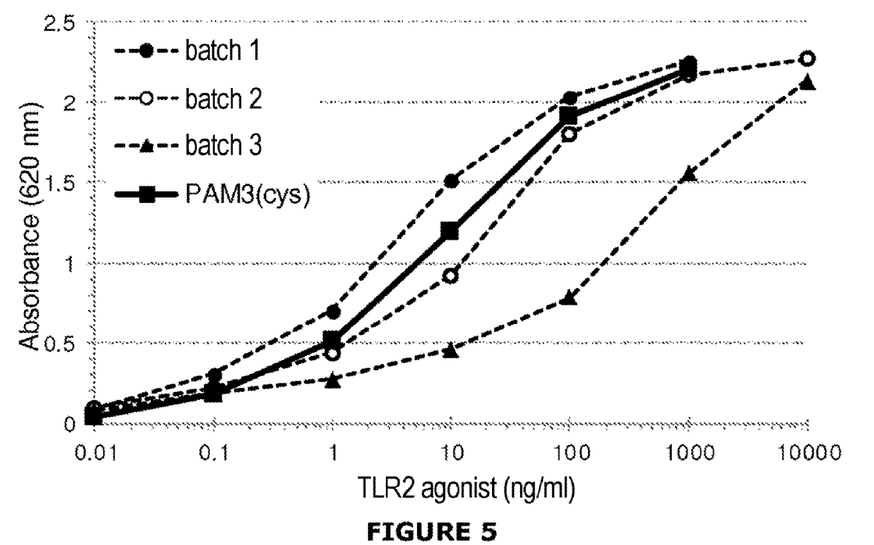
FIG. 5: Comparison of the responses induced by different batches of PGNs of *S. aureus* and by PAM3(cys) in the HEK-Blue™-hTLR2 cells.

To test this hypothesis, the responses of the HEK-TLR2 cells, induced by three separate batches of PGNs extracted from *S. aureus:* 2 Sigma batches (Cat No 77140: batch 1, 0001442777; batch 2, BCBH7886V) and 1 InvivoGen batch (# tlrl-pgnsa), were compared to those induced by PAM$_3$ (cys) (FIG. 5).

The results show variability of reactivity between the three batches of PGNs. Indeed, the EC50 values are 4, 20 and 400 ng/ml respectively for the three batches. These data indicate that there is a risk that PGNs extracted from the same bacterial species might show differences in reactivity, even if the batches were obtained from the same supplier and were in theory extracted by the same procedure. As expected, the cells show strong reactivity with respect to PAM$_3$(cys), with an EC50 of 8 ng/ml.

Figure 6:
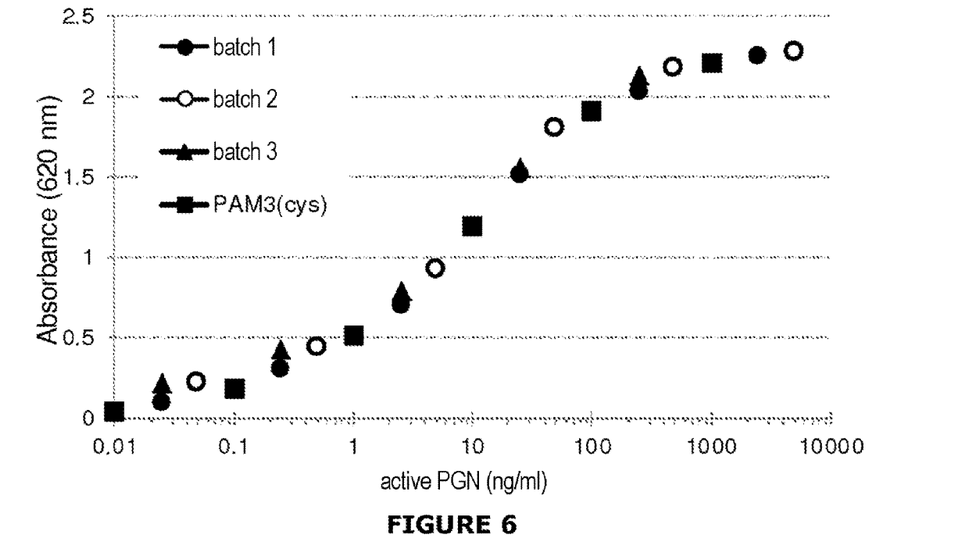
FIG. 6: Response of the HEK-Blue™-hTLR2 cells as a function of the corrected PGN concentrations.

Each batch of PGN may be calibrated relative to PAM$_3$(cys) by comparing the slopes of the linear portions of each dose-response curve, and by calculating a correction factor for superimposing the curves of the PGNs on that of PAM$_3$(cys). In the example presented in FIG. 6, the correction factors were estimated at 0.4, 2 and 40 for batches 1, 2 and 3, respectively. This means that 2.5 times less PGN from batch 1 is required for obtaining responses identical to those induced by PAM$_3$(cys), but 2 times more PGN from batch 2 and 40 times more PGN from batch 3. After correcting the raw quantities of PGN, it can be seen that all the points are aligned on one and the same curve, which is superimposed on that obtained with PAM3(cys) (FIG. 6). The use of this internal standard therefore makes it possible to obtain corrected concentrations for all the batches of PGN and to establish a dose-response curve calibrated for "active" PGN.

Figure 7:
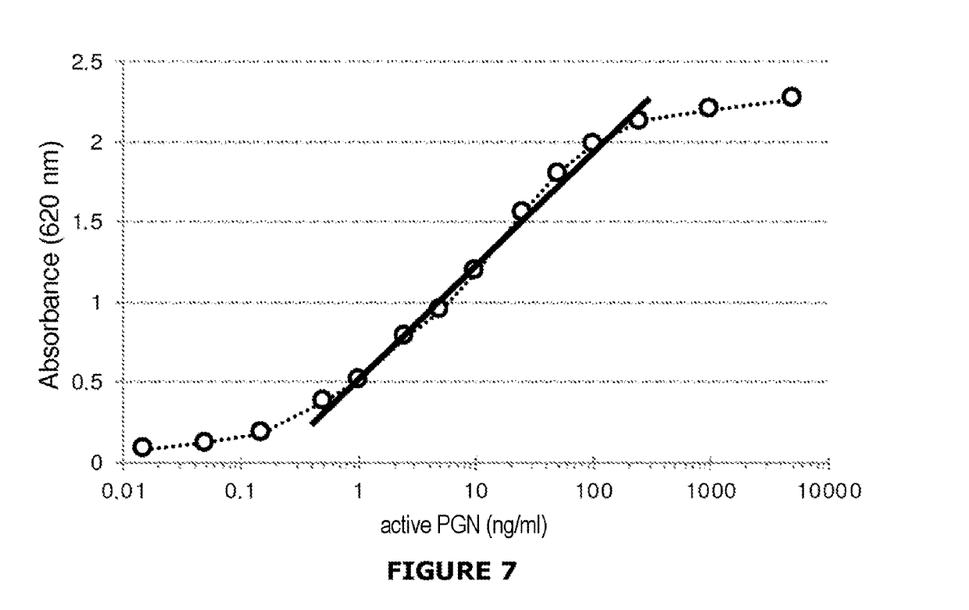
FIG. 7: Calibration curve of the response of the HEK-Blue™-hTLR2 cells as a function of the corrected active PGN concentrations.

By applying this method, the standard curve of response of the HEK-TLR2 cells has a detection threshold of 0.07 ng/ml (i.e. 2 ng/g of glucose polymers) and a zone of linearity for concentrations of active PGN of between 0.3 and 200 ng/ml (i.e. between 8 and 5400 ng/g of glucose polymers). (FIG. 7)

2. Enzymatic Treatment of the Samples of Glucose Polymers

The aim of the enzymatic treatment by the lysozyme is to fragment and/or disaggregate the PGNs contained in the sample, so as to make them capable of inducing an inflammatory response via the TLR2 receptor. In particular, the enzymatic treatment of the sample causes a partial depolymerization of the PGNs to generate soluble PGNs of sizes of between 30 and 5000 kDa, especially of a size of approximately 120 kDa. However, the enzymatic treatment must not affect the capacity of the PGNs to interact with the TLR2 receptors. It is preferably optimized for releasing a maximum amount of soluble PGNs capable of interacting with TLR2 and for storing a maximum amount of PGN already active on TLR2.

Tests of enzymatic treatments were carried out on four standard samples:

(1) a preparation of uncontaminated maltodextrin (reference P-11.11), (2) a preparation of P-11.11 maltodextrin, artificially contaminated with a sub-optimal dose of PGN from *S. aureus* (20 ng/ml final) (referred to as P-11.11+PGN), (3) a preparation of contaminated icodextrin (reference I-209J), and (4) a glucose polymer matrix (reference E1242).

|  | P-11.11 | I-E209J | E1242 |
|---|---|---|---|
| LAL assay LPS (EU/g) | <0.15 | 0.6 | 2.4 |
| SLP-HS assay PGN (ng/g) | <3 | 393 | 21 |

The treatments were carried out on 37% (weight/volume) solutions of glucose polymers. The solutions were then diluted to $\frac{1}{10}^{th}$ in the presence of the cells, by adding 20 μl of the solution to be tested to 180 μl of cell suspension.

The lysozyme used in these experiments is sold by Euromedex (ref: 5934; origin: egg white; activity: 25 000 units/mg).

Figure 8:
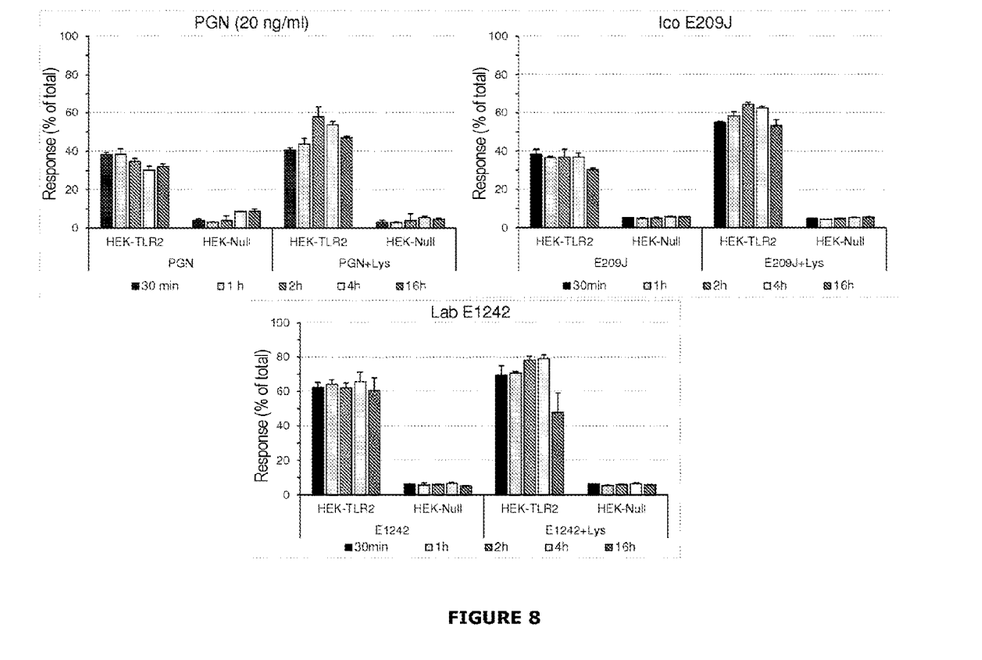
FIG. 8: Effect of the duration of treatment by the lysozyme on the cellular responses induced by the samples of glucose polymers.

The first tests were carried out by incubating preparations of P-11.11 maltodextrin contaminated with PGN (20 ng/ml), I-209J icodextrin or 1920-E1242 lab matrix, in the presence of lysozyme at a concentration of 250 U/ml (10 μg/ml). The treatment was carried out at 37° C. for times varying from 30 min to 16 h (FIG. 8). After stimulating the cells, the results show that the enzymatic treatment increases the reactivity of the PGNs with respect to the HEK-TLR2 cells. Moreover, no response is observed in the HEK-Null cells, which indicates that the treatment by the lysozyme does not have a cytotoxic effect.

The increase in the cellular response induced by the lysozyme is observed for short time periods, with optimal effect at 2 h of treatment. On the contrary, a longer hydrolysis time reduces the cellular response. This observation indicates that prolonged treatment in the presence of lysozyme causes too great a depolymerization of the PGNs, which reduces their capacity to interact with the TLR2 receptors.

Figure 9:
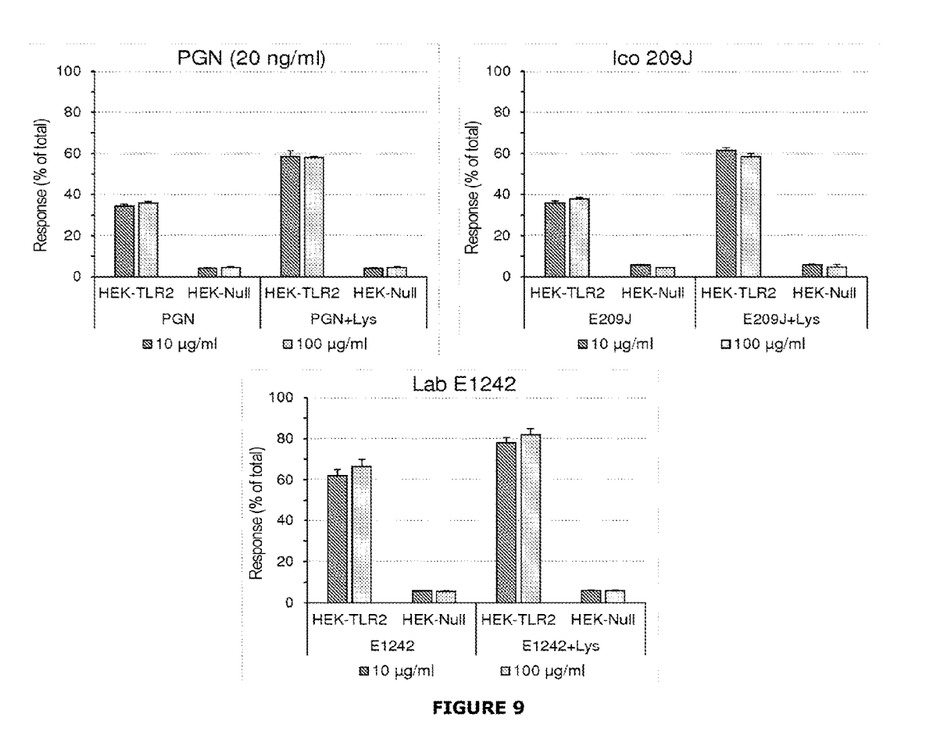
FIG. 9: Comparison of the cellular responses induced by the samples of glucose polymers after treatment by 10 and 100 μg/ml of lysozyme.

The experiments were then reproduced with the same samples, but using the lysozyme at concentrations of 10 and 100 μg/ml (FIG. 9). After 2 h of treatment at 37° C., no significant difference in the cellular responses is observed between the two concentrations of 10 and 100 μg/ml. Indeed, the enzymatic treatments similarly increase the reactivity of the PGNs for the HEK-TLR2 cells, and no cytotoxicity is observed in the HEK-Null cells, even at the higher lysozyme concentration.

These results show that a treatment by the lysozyme at a concentration of 250 U/ml for 2 h at 37° C. is effective for bringing about partial depolymerization of the PGNs present in samples of glucose polymer and for increasing their reactivity with respect to the HEK-TLR2 cells.

In conclusion, under the optimal conditions described above, a treatment by the lysozyme is effective for increasing the reactivity of the PGNs present in preparations of glucose polymers.

Depending on the type of PGN and the nature of the sample of glucose polymer (end product versus matrix derived from a process step), the activating effect brought about by the enzymatic treatment increases the reactivity of the HEK-TLR2 cells by a factor of up to 1.5. Thus, this treatment is particularly suited for converting all the traces of PGN present in samples to "active" PGN, and for allowing their biological assay.

The invention claimed is:

1. A method of assaying peptidoglycans (PGNs) in a sample of glucose polymer, comprising:

a) enzymatic treatment of the sample of glucose polymer by a lysozyme, wherein the treatment of the sample comprises incubation of lysozyme at a concentration of approximately 250 U/ml in the sample at a glucose polymer concentration of 37.5% (weight/volume) for 2 h at a temperature of 37° C.;

b) bringing the treated sample or a dilution thereof into contact with a recombinant cell expressing an exogenous TLR2 receptor (Toll-like Receptor 2) and a reporter gene under the direct dependence of the signaling pathway associated with the TLR2 receptor, the reporter gene coding for a fluorescent;

c) measuring the reporter gene signal; and d) determining the amount of PGN in the sample using a calibration curve of the correspondence between the amount of PGN and the intensity of the reporter gene signal.

2. The method as claimed in claim 1, wherein the enzymatic treatment of the sample fragments and disaggregates the PGNs contained in the sample so as to make them capable of activating the TLR2 receptor.

3. The method as claimed in claim 1, wherein the enzymatic treatment of the sample generates PGNs having a size of approximately 120 kDa.

4. The method as claimed in claim 1, wherein the treatment of the sample comprises incubation of lysozyme at a concentration of approximately 250 to 2500 U/ml in the sample at a glucose polymer concentration of 37.5% (weight/volume) for 30 minutes to 16 h at a temperature of 37° C.

5. The method as claimed in claim 1, wherein the reporter gene is a secreted alkaline phosphatase.

6. The method as claimed m claim 1, wherein the cell IS a cell of the HEK-Blue™ hTLR2 line.

7. The method as claimed in claim 1, wherein the calibration curve of the correspondence between the amount of PGN and the intensity of the reporter gene signal is set up with an internal standard that is an agonist of TLR2.

8. The method as claimed in claim 7, wherein said agonist of TLR2 is PAM3 Cys-Ser-(Lys)4 trihydrochloride.

9. The method as claimed in claim 1, wherein the sample is diluted, if necessary, so as to generate a signal of the reporter gene corresponding to the linear portion of the calibration curve.

10. The method as claimed in claim 1, wherein the sample is a sample of a solution of icodextrin.

* * * * *